United States Patent [19]

Kawazi et al.

[11] Patent Number: 5,068,103

[45] Date of Patent: Nov. 26, 1991

[54] SALBUTAMOL-CONTAINING PLASTER AND METHOD OF PRODUCING SAME

[75] Inventors: Toshikuni Kawazi; Masahiro Ono; Nobuko Inoue, all of Kagawa, Japan

[73] Assignees: Teikoku Seiyaku Kabushiki Kaisha, Kagawa, Japan; Chiesi Farmaceutici S.p.A., Parma, Italy

[21] Appl. No.: 241,458

[22] Filed: Sep. 8, 1988

[30] Foreign Application Priority Data

Sep. 8, 1987 [JP] Japan .................................. 62-224487

[51] Int. Cl.$^5$ ...................... A61K 31/74; A61K 31/78; A61K 9/70; A61K 31/135
[52] U.S. Cl. ......................................... 424/81; 424/78; 424/443; 514/653
[58] Field of Search ................... 514/653; 424/78, 443, 424/81

[56] References Cited

U.S. PATENT DOCUMENTS

| | | | |
|---|---|---|---|
| 4,568,343 | 2/1986 | Leeper et al. | 514/552 |
| 4,755,384 | 7/1988 | Mallasz | 424/443 |
| 4,755,525 | 7/1988 | Markwell et al. | 514/394 |

FOREIGN PATENT DOCUMENTS

| | | |
|---|---|---|
| 138124 | 10/1979 | Japan . |
| 35633 | 3/1980 | Japan . |
| 20515 | 2/1981 | Japan . |
| 209217 | 12/1982 | Japan . |
| 25320 | 2/1984 | Japan . |

OTHER PUBLICATIONS

Merck Index, Tenth Edition, p. 206 (1983).
Chem Abst, 109:98852w (1988), Zupon et al.

*Primary Examiner*—Frederick E. Waddell
*Assistant Examiner*—Zuhreh A. Fay
*Attorney, Agent, or Firm*—Oblon, Spivak, McClelland, Maier & Neustadt

[57] ABSTRACT

A plaster, which can be used in the prevention of attacks of bronchial asthma and in the treatment of bronchitis, comprises an adhesive base composition comprising a macromolecular substance and a sequestering agent and containing salbutamol, and a support for supporting the adhesive base composition spread thereon, and a method of producing the plaster are provided.

9 Claims, 3 Drawing Sheets

SALBUTAMOL-CONTAINING PLASTER AND METHOD OF PRODUCING SAME

BACKGROUND OF THE INVENTION

This invention relates to a plaster for achieving percutaneous absorption of salbutamol.

Salbutamol [1-(4-hydroxy-3-hydroxymethylphenyl)-2-(tert-butylamino)ethanol] is a beta-adrenergic drug. It acts strongly on beta-two ($\beta_2$) receptors on the bronchial muscle. It is used, generally in the form of sulfate, as a prophylactic agent for bronchial asthma, infantile asthma and the like or as a therapeutic agent for bronchitis and so forth.

In the prior art, this drug is administered to patients by the oral route in the form of tablets, syrups, inhalations (aerosols), etc.

However, oral administration of said drug has the following problems:

(1) Since the duration of the effect of salbutamol administration is generally about 6 hours, three or four administrations are required daily for the prevention of attacks. It is difficult to prevent asthmatic attacks while the patient is asleep or immediately after the patient's getting up early in the morning.

(2) It is difficult to administer the drug during an asthmatic attack.

(3) When the drug is absorbed through the digestive tract, the drug absorption may vary depending on the pH within the gastrointestinal tract and the extent of food intake. In addition, since the first-pass effect is great, an excessive dose may possibly cause palpitation, tachycardia, arrhythmia or blood pressure fluctuation due to sympathetic excitation or, furthermore, may possibly induce side effect, such as headache, dizziness, drowsiness, anorexia and nausea.

BRIEF SUMMARY OF THE INVENTION

Accordingly, it is an object of the invention to provide a salbutamol-containing plaster with which even one single application per day can allow continuous percutaneous absorption of salbutamol and maintenance of its blood concentration at least at a minimum effective level over a prolonged period of time and thereby can result in continued production of the desired pharmacological effects without occurrence of any significant side effect.

DETAILED DESCRIPTION OF THE INVENTION

Figure 1:
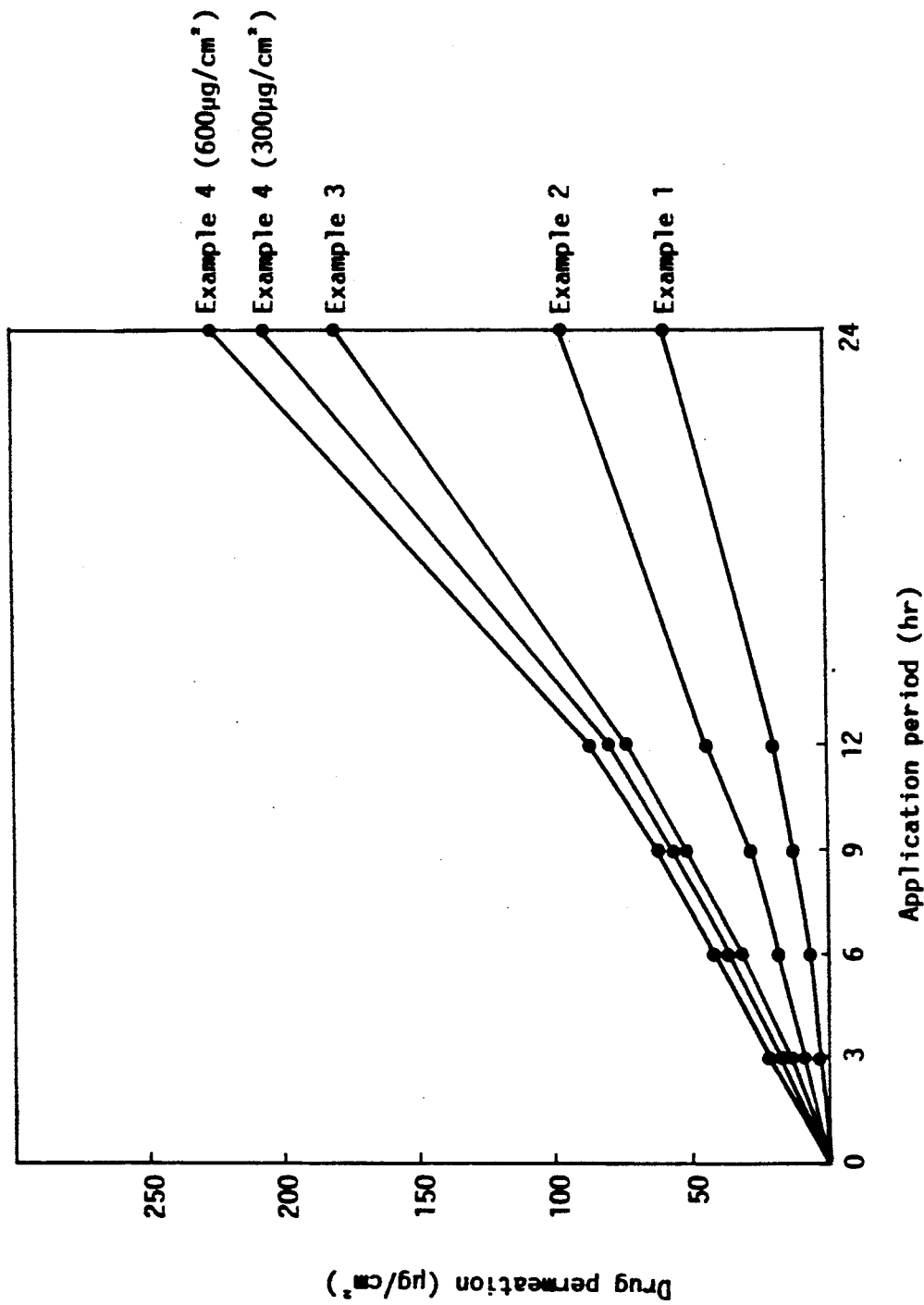
FIG. 1 graphically shows the relation between the plaster application period and the percutaneous drug permeation, FIG. 2 graphically shows the relation between the plaster application period and the percent inhibition of histamine-induced bronchoconstriction.

The present inventors felt the necessity of solving the above problems and made investigations in an attempt to develop a plaster for salbutamol absorption by another route than the prior art one, namely by the percutaneous route. As a result of their intensive investigations focused on the realization of continuous percutaneous drug absorption by making use of drug inclusion and sustained release properties of macromolecular substances, the present inventors have now established a satisfactory means of achieving the above object and have thus completed the present invention. The invention consists in that salbutamol is incorporated in an adhesive preparation containing a macromolecular substance and a metal sequestering agent.

In the following, the above-mentioned essential constituents and other components are described in more detail. First, the macromolecular substance is able to include salbutamol, among others, within cavities formed by crossed molecular chains and at the same time allow gradual diffusion of salbutamol in that inclusion state and stable release of the same from the cavities. As a result, the drug efficacy can be maintained for a prolonged period of time. The macromolecular substance to be used in accordance with the invention may be either a natural macromolecular substance or a synthetic macromolecular substance. It may be adhesive or nonadhesive. When, however, a nonadhesive macromolecular substance is used, it is recommendable to incorporate an adhesive component to attain a satisfactory level of adhesiveness. Examples of such macromolecular substance are natural rubber, polyisoprene, polybutadiene, styrene-isoprene-styrene block copolymers, polyacrylic esters, polymethacrylic esters, acrylic ester-methacrylic ester copolymers, acrylic acid-acrylic ester-vinyl acetate copolymers and petroleum resins. Among acrylic polymers, those obtained by copolymerising not more than 10% of acrylic acid, 60-100% of an acrylic ester and not more than 20% of vinyl acetate are advantageously used.

These macromolecular substances may be used either singly or in combination of two or more. When a natural rubber is used as the macromolecular substance, it is recommendable to use a composition composed of 30-70% (% by weight; hereinafter the same shall apply) of the rubber component, 30-60% of a tackifier resin, not more than 20% of a softening agent and 0.01-2% of an antioxidant. When a styrene-isoprene-styrene block copolymer is used as the macromolecular substance, it is recommendable to use a composition composed of 20-40% of said copolymer, 30-60% of a tackifier resin, 5-20% of a liquid rubber and 0.01-2% of an antioxidant.

As the tackifier resin mentioned above, there may be mentioned, for example, alicyclic saturated hydrocarbon petroleum resins, rosin, rosin glycerol ester, hydrogenated rosin, hydrogenated rosin glycerol ester, hydrogenated rosin pentaerythritol ester, cumaroneindene resins, polyterpenes, terpene-phenolic resins, cycloaliphatic hydrocarbon resins, alkyl aromatic hydrocarbon resins, hydrocarbon resins, aromatic hydrocarbon resins, and phenolic resins. The antioxidant includes, but is not limited to, dibutylhydroxytoluene (BHT) and the softening agent includes, but is not limited to, liquid paraffin and petrolatum.

The above-mentioned components generally contain trace amounts of metals as impurities, which can promote decomposition of salbutamol during storage and decrease the storage stability of plaster products. In accordance with the invention, a metal sequestering agent is incorporated into the adhesive base composition, whereby metals are seized and held by said agent and accordingly promoted decomposition of the pharmacologically active component can be avoided even during a long period of storing of the plasters. The sequestering agent to be used in accordance with the invention includes, among others, EDTA, potassium polyphosphate, sodium polyphosphate, potassium metaphosphate, sodium metaphosphate, dimethylglyoxime, 8-hydroxyquinoline, nitrilotriacetic acid, dihydroxyethylglycine, gluconic acid, citric acid and tartaric acid. These are recommendably used in an amount of 0.01-2%.

It is necessary to increase the bioavailability of the pharmacologically active ingredient salbutamol by adjusting the quantity thereof relative to the adhesive base preparation. From this viewpoint, it is preferable that the amount of salbutamol be 1-6% based on the adhesive base preparation. When the salbutamol amount is less than 1%, salbutamol included or seized by the macromolecular substance can hardly be released, so that only a poor drug efficacy will be obtained. On the other hand, incorporation in an amount exceeding 6% will not result in further increased drug efficacy. In the practice of the invention, addition of a solvent for salbutamol in an adequate amount is optional. Examples of the solvent are crotamiton, higher fatty acids such as oleic acid and myristic acid, and polypropylene glycol, among others. The combination of these adhesive base preparation constituents should desirably be selected while the control of drug release and the inhibition of skin irritation are taken into consideration. In the practice of the invention, a skin irritation reducing agent, such as vitamin E, glycyrrhetic acid or diphenhydramine, may be added.

The adhesive base preparation components should be used in such relative amounts that can give satisfactory adhesive characteristics (tack, adhesive strength, cohesion strength) and satisfactory percutaneous absorption, which are fundamental to the final dosage form preparation. The allowable addition levels given above for the respective components have been established from such point of view.

The plaster according to the invention can be produced by incorporating salbutamol in the above-mentioned adhesive base composition and spreading the resultant preparation upon a support so as to form a drug-containing layer on said support.

The amount of the salbutamol-containing adhesive preparation to be spread on the support is generally, but not limited to, 40-500 g/m$^2$.

The support to be used in the practice of the invention should desirably be a thin one made of a soft and flexible material which can change its form or shape in agreement with the motion of the carrier (person). It includes nonwoven fabrics, woven fabrics, flannels and spandex fabrics, and laminates derived from these materials and a polyethylene film, an ethylene-vinyl acetate film, a polyurethane film or the like, as well as polyvinyl chloride films, polyethylene films, polyurethane films, aluminum deposited films and so forth, either as they are or in the form of composite films derived therefrom. The support may be perforated when diffusion of perspiration moisture should be taken into consideration.

The following examples are further illustrative of the present invention but by no means limitative of the scope thereof. It should be understood that all modifications that can be made in the light of the disclosure made hereinabove and hereinbelow fall within the scope of the present invention.

In the following examples, the adhesive base preparation were spread upon a release paper always in an amount (after drying) of 100 g/m$^2$, or in a salbutamol amount (after drying) of 600 μg/cm$^2$. In Example 4 alone, however, the adhesive preparation was used in an amount (after drying) of 50 g/m$^2$, or in a salbutamol amount (after drying) of 300 μm/cm$^2$.

| Example 1 | |
|---|---|
| Natural rubber | 29.5 parts |
| Styrene-butadiene rubber | 13 parts |
| Ester gum | 20 parts |
| Hydrogenated rosin resin | 20 parts |
| BHT | 1 parts |

The above components were dissolved in toluene to a solid content of 30%.

| | |
|---|---|
| Salbutamol | 6 parts |
| Myristic acid | 10 parts |
| EDTA | 0.5 part |

Then, the above three components were added to the solution, and the resultant mixture was mixed and stirred and then spread upon a release paper, followed by drying. After lamination of a polyethylene film, the whole was cut to a desired size to give test specimens.

| Example 2 | |
|---|---|
| Styrene-isoprene-styrene block copolymer | 20 parts |
| Alicyclic saturated hydrocarbon petroleum resin (trademark "Arkon P-100; Arakawa Chemical Industries) | 50 parts |
| Liquid rubber (trademark "Kuraprene LIR-50; Kuraray Isoprene Chemical) | 12.5 parts |
| BHT | 1 part |

The above components were melted and kneaded in a kneader. To the thus-obtained mixture were added the following:

| | |
|---|---|
| Salbutamol | 6 parts |
| Myristic acid | 10 parts |
| EDTA | 0.5 part |

After further kneading, the resultant mixture was spread on a release paper and dried. Thereafter, the same procedure as in Example 1 was followed to give test specimens.

EXAMPLE 3

Test specimens were prepared in the same manner as in Example 2 using the same components in the same amounts as used in Example 2 except that hydrogenated rosin resin was used in lieu of the alicyclic saturated hydrocarbon petroleum resin.

| Example 4 | |
|---|---|
| Acrylic acid | 6.0 parts |
| 2-Ethylhexyl acrylate | 63.5 parts |
| Vinyl acetate | 14.0 parts |
| Azobisisobutyronitrile | 0.1 part |

The above components were mixed and copolymerized in ethyl acetate to give an acrylic adhesive solution in ethyl acetate, which had a solid content of 40%.

To this solution were added the following:

| | |
|---|---|
| Salbutamol | 6.0 parts |
| EDTA | 0.4 part |

| | |
|---|---|
| -continued | |
| Myristic acid | 10.0 parts |

The whole mixture was kneaded, spread on a release paper and dried. Thereafter, the same procedure as in Example 1 was followed to give test specimens.

The test specimens obtained in Example 1-4 were submitted to the following tests (Test 1 and 2).

Test 1

The quantity of salbutamol permeating the rat abdominal skin mounted on a Franz diffusion cell was determined at timed intervals by HPLC (high-performance liquid chromatography).

Thus, a disk, 2.5 cm in diameter, was punched out from each specimen and applied to the rat skin. The disk-rat skin assembly was mounted on the diffusion cell, and the salbutamol permeation into the receptor side (phosphate buffer, pH 6.8) was determined at hours 2, 4, 8, 12, 16 and 24. The results thus obtained are shown in FIG. 1.

As is evident from the results shown in FIG. 1, the plasters according to the invention showed good and continuous percutaneous salbutamol permeation over 24 hours of continued application.

Test 2

Hair was removed from the abdominal region of beagle dogs under anesthesia. A test specimen, cut to a size of 5 cm×5 cm, was applied to the abdominal area and tested by the Konzett-Rossler method for the inhibition of bronchoconstriction induced by intravenous administration of 5 μg/kg of histamine. In a comparative example, a salbutamol tablet was administered orally (500 μg/kg, p.o.).

Figure 2:
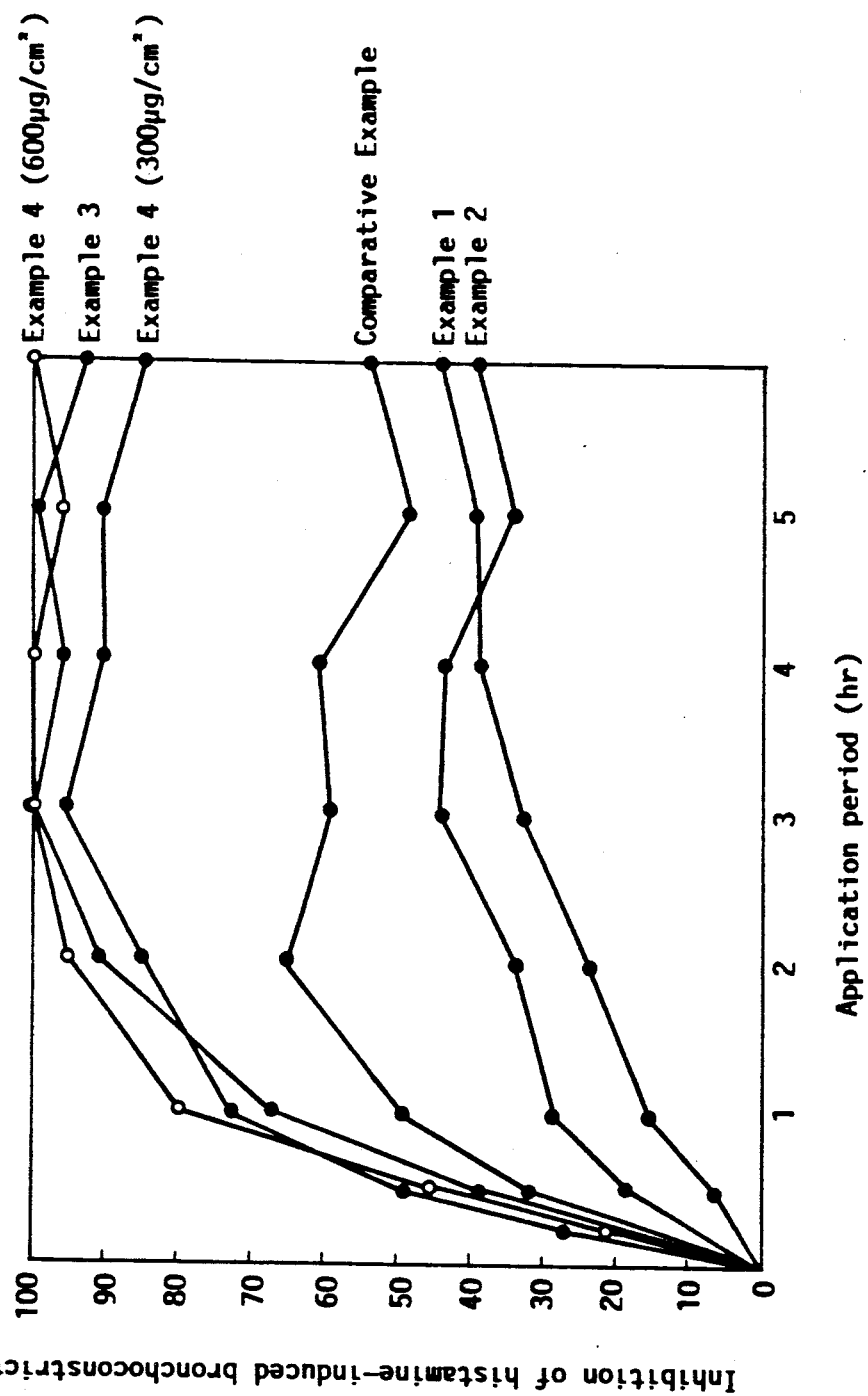

The results thus obtained are shown in FIG. 2. As is evident from FIG. 2, the products according to the invention showed excellent bronchoconstriction inhibiting activity.

Then, for evaluating the effect of incorporation of sequestering agents, test specimens were prepared according to the same formulations as used in Examples 1, 3 and 4 except that the sequestering agent was omitted. These specimens (Comparative Examples 1, 3 and 4) and the specimens of Examples 1, 3 and 4 were submitted to a salbutamol stability test. Each test specimen was wrapped up in an aluminum foil-polyethylene laminate film and stored under temperature-humidity conditions of 40° C. and 75% RH. On each measurement day, each sample was taken out and assayed for residual salbutamol by HPLC.

Figure 3:
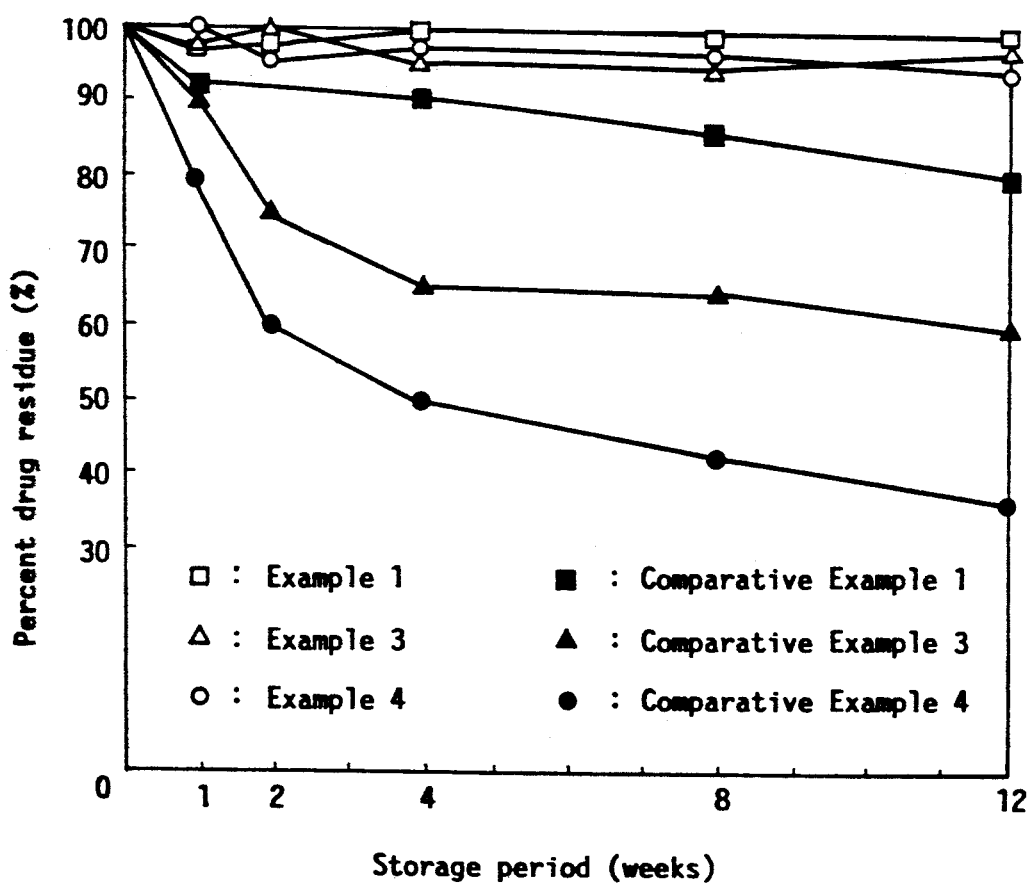
FIG. 3 shows results of an experiment which demonstrate the drug stabilizing effect of sequestering agents.

The results thus obtained are shown in FIG. 3.

As is evident from FIG. 3, the plasters according to the invention showed a residual salbutamol percentage exceeding 90% even after a considerably long period of storage. Thus, the stabilizing effect of the sequestering agent incorporated was remarkable as compared with the comparative examples.

We claim:

1. A salbutamol-containing plaster which comprises an adhesive preparation containing a macromolecular substance selected from the group consisting of natural rubber, polyisoprene, polybutadiene, styrene-isoprene-styrene block copolymers, polyacrylic esters, polymethacrylic esters, acrylic ester-methacrylic ester copolymers, acrylic acid-acrylic ester-vinyl acetate copolymers and petroleum resins in an amount of 20–70%, and a metal ion sequestering agent selected from the group consisting of ethylene diamine tetraacetic acid, potassium polyphosphate, sodium polyphosphate, potassium metaphosphate, sodium metaphosphate, dimethylglyoxime, 8-hydroxyquinoline, nitrilotriacetic acid, dihydroxyethylglycine, gluconic acid, citric acid and tartaric acid in an amount of 0.01–2%, and an effective amount of salbutamol or a pharmaceutically acceptable salt thereof in an amount of 1–6% incorporated in said adhesive preparation, the salbutamol-containing adhesive preparation being spread on a support to form a salbutamol-bearing layer.

2. A salbutamol-containing plaster as claimed in claim 1, wherein the adhesive preparation contains a tackifier resin.

3. A salbutamol-containing plaster as claimed in claim 1, wherein the adhesive preparation contains a softening agent.

4. A salbutamol-containing plaster as claimed in claim 1, wherein the macromolecular substance contains double bonds and wherein the adhesive preparation contains an antioxidant.

5. A salbutamol-containing plaster as claimed in claim 1, wherein salbutamol is contained in the salbutamol-bearing layer in an amount of 1–6% by weight and the sequestering agent in an amount of 0.01–2% by weight.

6. A salbutamol-containing plaster as claimed in claim 1, wherein the macromolecular substance is a copolymer of not more than 10% of acrylic acid, 60–100% of an acrylic ester and not more than 20% of vinyl acetate.

7. A salbutamol-containing plaster as claimed in claim 1, wherein the macromolecular substance is a natural rubber and wherein the adhesive preparation has the following composition:

| | |
|---|---|
| Natural rubber | 30–70% by weight |
| Tackifier resin | 30–60% by weight |
| Softening agent | Not more than 20% by weight |
| Antioxidant | 0.01–2% by weight |
| Sequestering agent | 0.01–2% by weight. |

8. A salbutamol-containing plaster as claimed in claim 3, wherein the macromolecular substance is a styrene-isoprene-styrene block copolymer which accounts for 20–40% by weight of the adhesive preparation and wherein the softening agent is a liquid rubber which accounts for 5–20% by weight of the adhesive preparation.

9. A method of producing salbutamol-containing plasters as claimed in claim 1, which comprises incorporating salbutamol in said adhesive preparation containing said macromolecular substance and said sequestering agent, each as an essential component, and spreading the salbutamol-containing adhesive preparation upon a support.

* * * * *